United States Patent [19]

Dwyer

[11] Patent Number: 5,599,001
[45] Date of Patent: Feb. 4, 1997

[54] STUFFED ANIMAL CONDUIT RETAINER

[76] Inventor: Joseph G. Dwyer, 3 Maple Dr., Catonsville, Md. 21228

[21] Appl. No.: 452,838

[22] Filed: May 30, 1995

[51] Int. Cl.$^6$ ................................................. A47G 1/16
[52] U.S. Cl. .......................... 248/505; 248/910; 248/915; 446/369; 446/382
[58] Field of Search ........................... 248/68.1, 74.2, 248/74.3, 500, 504, 505, 910, 915; 446/97, 99, 107, 227, 369, 370, 374, 382, 390

[56] References Cited

U.S. PATENT DOCUMENTS

| | | | |
|---|---|---|---|
| 3,448,539 | 6/1969 | Hartpence | 446/370 X |
| 3,977,121 | 8/1976 | Goldfarb et al. | 446/369 |
| 4,226,046 | 10/1980 | Delhome | 46/123 |
| 4,296,567 | 10/1981 | Kamar | 446/369 |
| 4,505,687 | 3/1985 | Munro | 446/385 X |
| 4,755,160 | 7/1988 | Autore | 446/369 |
| 4,809,938 | 3/1989 | Skinner et al. | 248/102 |
| 4,816,000 | 3/1989 | Narvaez et al. | 446/370 |
| 4,968,281 | 11/1990 | Smith et al. | 446/369 |
| 5,026,315 | 6/1991 | Chap | 446/369 X |
| 5,516,314 | 5/1996 | Anderson | 446/374 |

*Primary Examiner*—Carl D. Friedman
*Assistant Examiner*—Yvonne Horton-Richardson

[57] ABSTRACT

A retainer for maintaining a plurality of conduits in a desired orientation. The inventive device is freestanding on any given horizontal surface. A plurality of engaging assemblies radiate from the mounting assembly for coupling to I.V. lines to maintain the lines in a desired orientation.

1 Claim, 2 Drawing Sheets

STUFFED ANIMAL CONDUIT RETAINER

BACKGROUND OF THE INVENTION

1. Field of the Invention

The present invention relates to conduit holders and more particularly pertains to an stuffed animal conduit retainer for maintaining a plurality of conduits in a desired orientation.

2. Description of the Prior Art

The use of conduit holders is known in the prior art. More specifically, conduit holders heretofore devised and utilized are known to consist basically of familiar, expected and obvious structural configurations, notwithstanding the myriad of designs encompassed by the crowded prior art which have been developed for the fulfillment of countless objectives and requirements.

Known prior art conduit holders include U.S. Design Pat. No. 317,799; U.S. Design Pat. No. 253,668; U.S. Design Pat. No. 276,638; U.S. Design Pat. No. 316,734; U.S. Pat. No. 4,749,195; and U.S. Pat. No. 4,214,750.

While these devices fulfill their respective, particular objectives and requirements, and aforementioned patents do not disclose a stuffed animal conduit retainer for maintaining a plurality of conduits in a desired orientation, and a plurality of engaging assemblies radiating from the mounting assembly for coupling to I.V. lines and other conduits to maintain the conduits in a desired orientation.

In these respects, the stuffed animal conduit retainer according to the present invention substantially departs from the conventional concepts and designs of the prior art, and in so doing provides an apparatus primarily developed for the purpose of maintaining a plurality of conduits in a desired orientation.

SUMMARY OF THE INVENTION

In view of the foregoing disadvantages inherent in the known types of conduit holders now present in the prior art, the present invention provides a new stuffed animal conduit retainer construction wherein the same can be utilized for maintaining a plurality of conduits in a desired orientation. As such, the general purpose of the present invention, which will be described subsequently in greater detail, is to provide a new stuffed animal conduit retainer apparatus and method which has many of the advantages of the conduit holders mentioned heretofore and many novel features that result in a stuffed animal conduit retainer which is not anticipated, rendered obvious, suggested, or even implied by any of the prior art conduit holders, either alone or in any combination thereof.

To attain this, the present invention generally comprises a retainer for maintaining a plurality of conduits in a desired orientation. A plurality of engaging assemblies radiate from the mounting assembly for coupling to I.V. lines to maintain the lines in a desired orientation.

There has thus been outlines, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new stuffed animal conduit retainer apparatus and method which has many of the advantages of the conduit holders mentioned heretofore and many novel features that result in a stuffed animal conduit retainer which is not anticipated, rendered obvious, suggested, or even implied by any of the prior art conduit holders, either alone or in any combination thereof.

It is another object of the present invention to provide a new stuffed animal conduit retainer which may be easily and efficiently manufactured and marketed.

It is a further object of the present invention to provide a new stuffed animal conduit retainer which is of a durable and reliable construction.

An even further object of the present invention is to provide a new stuffed animal conduit retainer which is susceptible of a low cost of manufacture with regard to both materials and labor, and which accordingly is then susceptible of low prices of sale to the consuming public, thereby making such stuffed animal conduit retainers economically available to the buying public.

Still yet another object of the present invention is to provide a new stuffed animal conduit retainer which provides in the apparatuses and methods of the prior art some of the advantages thereof, while simultaneously overcoming some of the disadvantages normally associated therewith.

Still another object of the present invention is to provide a new stuffed animal conduit retainer for maintaining a plurality of conduits in a desired orientation.

Yet another object of the present invention is to provide a new stuffed animal conduit retainer, and a plurality of engaging assemblies radiating from the mounting assembly for coupling to I.V. lines to maintain the lines in a desired orientation.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in

3 which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
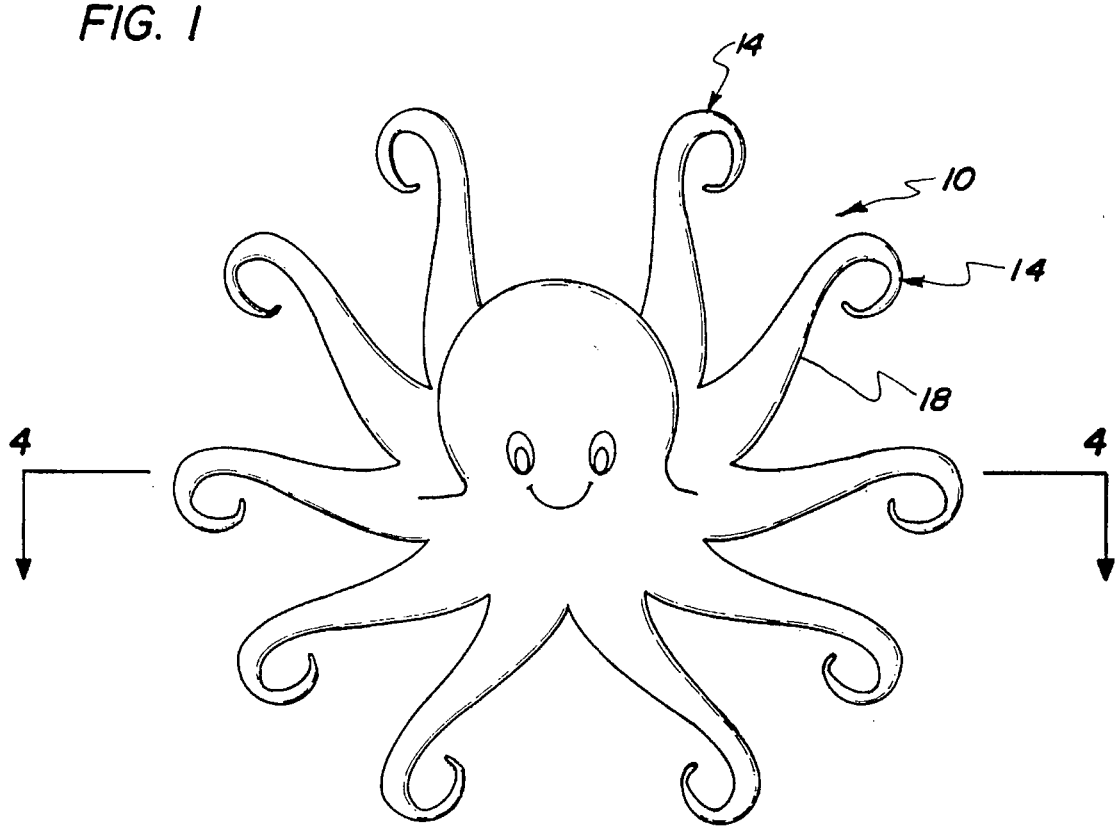
FIG. 1 is an isometric illustration of a stuffed animal conduit retainer according to the present invention.

With reference now to the drawings, and in particular to FIGS. 1–4 thereof, a new stuffed animal conduit retainer embodying the principles and concepts of the present invention and generally designated by the reference numeral 10 will be described.

Figure 2:
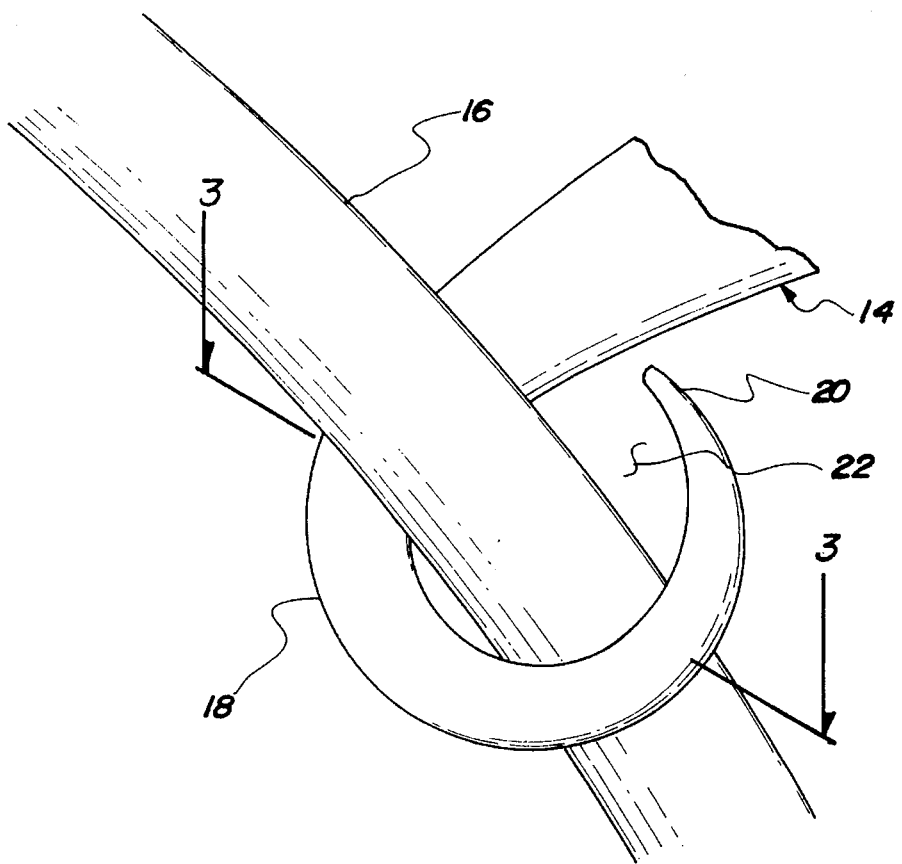
FIG. 2 is an enlarged isometric illustration of a portion of the present invention in use.

More specifically, it will be noted that the stuffed animal conduit retainer 10 comprising a plurality of engaging means 14 radiating from the conduit retainer 10 and are each operable to engage an individual conduit 16 as shown in FIG. 2 of the drawings so as to maintain a plurality of conduits in a desired orientation.

Figure 3:
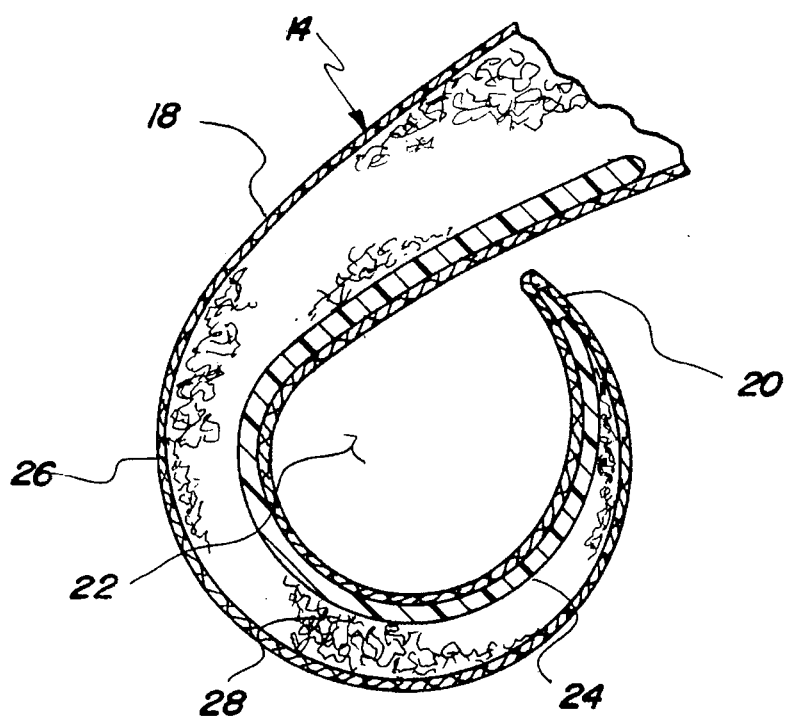
FIG. 3 is a cross-sectional view taken along line 3—3 of FIG. 2.

As best illustrated in FIGS. 2 and 3, it can be shown that each of the engaging means 14 of the present invention 10 preferably comprises an elongated projection 18 extending from the conduit retainer 10. Each of the elongated projections 18 includes a free outer end 20 which is curled back upon itself so as to define a receiving aperture 22 within which an individual conduit 16 can be positioned. The outer end 20 is resiliently biased into the closed configuration about the conduit 16 by a curved spring member 24 extending within a portion of the elongated projection 18. As shown in FIG. 3, the elongated projection 18 is preferably formed of an exterior web 26 having a stuffing material 28 secured therewithin. The curved spring member 24 is secured to an interior surface of the exterior web 26 proximal to the outer end 20 of the elongated projection 18 so as to cause the outer end 20 to bend back upon the elongated projection 18 to define the receiving aperture 22 through which the conduit 16 can be extended. By this structure, one or more conduits 16 can be easily coupled or decoupled from an individual one of the engaging means 14 as desired by an end user.

Figure 4:
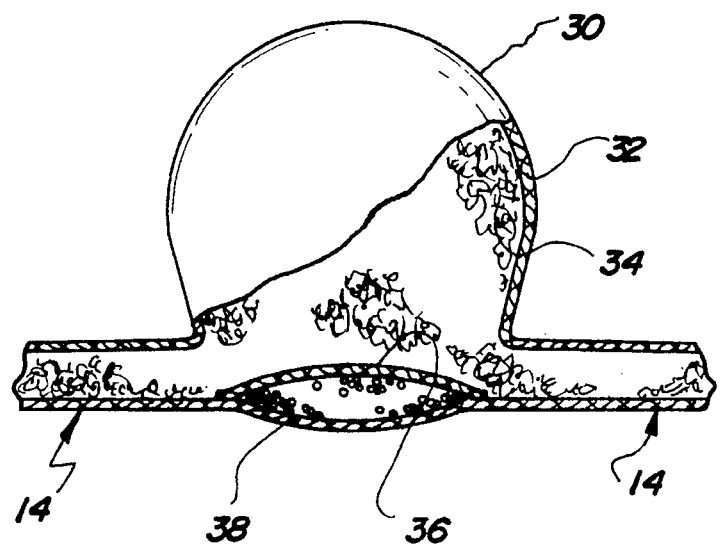
FIG. 4 is a partial cross-sectional view taken along line 4—4 of FIG. 1.

As best illustrated in FIG. 4, it can be shown that the conduit retainer 10 preferably comprises a weighted central body 30 shaped so as to resemble a body of an octopus. To this end, the weighted central body 30 comprises an exterior web 32 shaped in a substantially spherical configuration and containing a volume of stuffing material 34 therewithin. A partition web 36 extends within a portion of the weighted central body 30 and operates to contain a volume of weight material 38 between the partition web 36 and an interior surface of a portion of the exterior web 32. By this structure, the weight material 38 causes a gravitationally induced frictional engagement between a lower surface of the weighted central body 30 and the horizontal surface upon which the device 10 is positioned so as to secure the same relative thereto. Preferably, the elongated projections 18 of the engaging means 14 cooperate with the weighted central body of the conduit retainer 10 so as to simulate an overall appearance of an octopus, as shown in FIG. 1 of the drawings.

In use, the stuffed animal conduit retainer 10 according to the present invention can be easily utilized for maintaining a plurality of conduits in a desired orientation. The present invention 10 allows fluid conduits such as I.V. lines or the like to be individually engaged to one of the engaging means 14 so as to preclude unintentional removal and/or entanglement of such conduits 16.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A stuffed animal conduit retainer for supporting medical conduits comprising:

a weighted central body gravitationally secured to a horizontal support surface and shaped to resemble a body of an octopus, the weighted central body comprises an exterior web shaped in a substantially spherical configuration and containing a volume of stuffing material therewithin;

a partition web extending across a portion of the weighted central body;

a volume of weight material positioned between the partition web and an interior surface of a portion of the exterior web of the weighted central body;

a plurality of engaging means radiating from the central body for engaging an individual conduit to maintain a plurality of conduits in a desired orientation, each engaging means comprises an elongated projection extending from the central body, each of the elongated projections including a free outer end which is curled back upon itself to define a receiving aperture having an individual conduit positioned within, the elongated projection being formed of an exterior web having a stuffing material secured therewithin; and a curved spring member extending within a portion of the elongated projection resiliently biasing the outer end into a normally constricted configuration, the curved spring member being secured to an interior surface of the exterior web proximal to the outer end of the elongated projection to cause the outer end to bend back upon the elongated projection to define the receiving aperture through which a conduit is positioned.

\* \* \* \* \*